United States Patent [19]

Sugimoto

[11] Patent Number: 4,621,050

[45] Date of Patent: Nov. 4, 1986

[54] PROCESS FOR THE PRODUCTION OF HUMAN COLONY-STIMULATING FACTOR

[75] Inventor: Kaname Sugimoto, Okayama, Japan

[73] Assignee: Kabushiki Kaisha Hayashibara Seibutsu Kagaku Kenkyujo, Okayama, Japan

[21] Appl. No.: 585,617

[22] Filed: Mar. 5, 1984

Related U.S. Application Data

[63] Continuation-in-part of Ser. No. 329,118, Dec. 9, 1981, abandoned.

[30] Foreign Application Priority Data

Dec. 31, 1980 [JP] Japan .............................. 55-185732

[51] Int. Cl.⁴ ..................... C12P 21/00; C12N 15/00; C12N 5/00; C12N 5/02
[52] U.S. Cl. ................................. 435/68; 435/172.2; 435/240; 435/241; 435/284; 435/948; 530/399; 935/106; 935/109
[58] Field of Search ............... 435/1, 6, 172.2, 172.3, 435/240, 241, 68, 948, 248, 284, 286; 436/548; 424/85, 86, 87; 260/112 B, 112 R; 935/106, 109; 530/399

[56] References Cited

U.S. PATENT DOCUMENTS

| | | | |
|---|---|---|---|
| 4,242,460 | 12/1980 | Chick et al. ........................ | 435/283 |
| 4,276,282 | 6/1981 | Sugimoto et al. .................. | 425/85 |
| 4,285,929 | 8/1981 | Sugimoto et al. .................. | 424/85 |
| 4,328,207 | 5/1982 | Sugimoto ............................ | 424/85 |
| 4,377,513 | 3/1983 | Sugimoto et al. .............. | 260/112 R |
| 4,383,034 | 5/1983 | Sugimoto ............................ | 435/70 |
| 4,383,035 | 5/1983 | Sugimoto ............................ | 435/70 |
| 4,383,036 | 5/1983 | Sugimoto ............................ | 435/70 |

OTHER PUBLICATIONS

Zeleznik, Production of Long Term Steroid-Producing Granulosa Cell Cultures by Cell Hybridization, *Endocrinology*, vol. 105, 1979, pp. 156-162.

Lewin, *Gene Expression*, vol. 2, John Wiley and Sons, New York, 1980, pp. 259-265.

Howard, M., et al., "T-Cell Hybridoma Secreting Hemopoietic Regulatory Molecules: Granulocyte-Macrophage and Eosinophil Colony-Stimulating Factors", *Cell*, vol. 18, pp. 993-999 (1979).

Asano et al., article (Detection and Assessment of Human Tumors ... ), *British Journal of Cancer*, vol. 41, 1980, pp. 689-694.

*Primary Examiner*—Sidney Marantz
*Assistant Examiner*—Patricia L. DeSantis
*Attorney, Agent, or Firm*—Browdy & Neimark

[57] ABSTRACT

A process for the mass production of hCSF, comprises cell fusion of human lymphoblastoid cells with any human cells capable of producing said substance, in vivo multiplication of the resultant hybridoma cells, using a non-human warm-blooded animal, and in vivo cultivation of the multiplied hybridoma cells to produce hCSF. The hCSF production according to the present process is much higher than that attained by conventional processes; thus, hCSF can be used in a sufficient amount in the prevention and treatment of human diseases.

25 Claims, No Drawings

PROCESS FOR THE PRODUCTION OF HUMAN COLONY-STIMULATING FACTOR

The present application is a continuation-in-part of parent application Ser. No. 329,118, filed Dec. 9, 1981, abandoned, the entire contents of which are hereby incorporated by reference.

DETAILED DESCRIPTION OF THE INVENTION

The present invention relates to a process for the production of human Colony-Stimulating Factor (hereinafter abbreviated as hCSF).

It is known that hCSF is a stimulatory hormone that stimulates the differentiation of human stem cells to leukocytes. Recently, irradiation and administration of carcinostatic agents have been in more and more frequent use in treating malignant diseases which are now regarded as a major cause of death. However, such therapies inevitably result in an undesirable decrease in leukocyte count and in a decrease in the physical resistance of the patient. Consequently, the continuation of such therapies in often rendered very difficult. The utilization of hCSF in combination with one or more of the above therapies would doubtlessly provide a more effective therapy for malignant diseases, as well as for leukemia, a disease which has been regarded as incurable.

As to hCSF production, although some possible ways are known for obtaining, such as, recovering hCSF from human secreta or certain human tissues through very complicated processes, or multiplying hCSF-producing human cells by in vitro tissue culture with culture medium containing essential nutrients or by in vivo transplantation of said cells to a non-human warm-blooded animal body previously immunosuppressed with antiserum or immunosuppressant and subjecting the resultant multiplied cells to induction, the hCSF preparation obtained by any of the above processes is usually immunologically inactive, and even if active, the level of hCSF in such preparation is extremely low. Due to such disadvantages, the substance is not in practical use despite the recognition of its great potentiality.

The present inventor has investigated processes to produce sufficient amounts of homogenous hCSF for medical applications, such as clinical and therapeutic uses. These efforts have resulted in the unexpected finding that hCSF production attained with the hybridoma cells formed by fusing human cells capable of producing hCSF with human lymphoblastoid cells usually leads to two to ten times higher yields than that attained with hCSF-producing cells alone, and further, when said hybridoma cells are multiplied in non-human warm-blooded animal bodies, the hCSF production of the hybridoma cells increases about two to 50-fold or higher than that attained with said hybridoma cells multiplied by in vitro tissue culture, or with human cells or human tumor cells that are capable of producing hCSF cultivated in vivo or in vitro. More precisely, the present invention relates to a process for the production of hCSF, characterized in fusing human lymphoblastoid cells with any human cells that are capable of producing hCSF, in multiplying said hybridoma cells by transplanting the hybridoma cells into a non-human warm-blooded animal body or by allowing the hybridoma cells to multiply with a device by which the nutrient body fluid of the animal is supplied to the hybridoma cells, and in allowing the multiplied hybridoma cells to release hCSF.

The process for the multiplication of human hybridoma cells according to the present invention provides a much higher yield of hCSF, requires no or much less nutrient medium containing expensive serum, and further renders the maintenance of the cell culture much easier than in the case of in vitro tissue culture. Particularly, any human lymphoblastoid cells introduced with the ability of producing hCSF by fusing said cells with hCSF-producing human cells, can be multiplied easily by transplanting said hybridoma cells into a non-human warm-blooded animal body, or by suspending said hybridoma cells in a diffusion chamber devised to recieve the nutrient body fluid supplied from the non-human warm-blooded host animal, and feeding the host animal in usual way while utilizing the nutrient body fluid supplied from the non-human warm-blooded animal. In addition, the process is characterized by the stabler and higher cell multiplication, and higher hCSF production per cell than any conventional processes, such as by transplanting any human normal cells or tumor cells that are capable of producing hCSF in an immunodefficient animal body, for example, nude mouse, to effect the multiplication of said cells in vivo, followed by cultivating said cells to produce hCSF, the hCSF production according to the present invention, by fusing human lymphoblastoid cells with the human cells capable of producing hCSF followed by multiplying said hybridoma cells in vivo, is usually two to ten fold or higher.

The hybridoma cells used in the present invention which can be obtained by fusing human cells capable of producing hCSF with human lymphoblastoid cells according to well known procedures, are able to produce hCSF and also are easily multipliable when transplanted into a non-human warm-blooded animal body.

As to the hCSF-producing human cells usable for the hybridization with human lymphoblastoid cells in the present invention, any human cells can be used according to the present invention so far as they have the ability of producing hCSF, without any special consideration to the cell origin. For example, lung cells, spleen cells, peripheral blood cells, leukocytes, fetal kidney cells, submaxillary gland cells, bone marrow cells, T-lymphocytes, B-lymphocytes, placental cells or uterus cells; tumor cells of the above mentioned cells transformed with virus, carcinogenic agent or radiation; malignant tumor cells derived from lung carcinoma, leukemia, lymphoma, uterus carcinoma, kidney carcinoma or gastric carcinoma patients; and also any established cell lines of the above mentioned cells can be used conveniently in the present invention.

As to the human lymphoblastoid cells to which the hCSF-producing ability is introduced from the cells capable of producing hCSF as described above, in the present invention, any human lymphoblastoid cells can be used so far as they form the hybridoma cells with said hCSF-producing human cells and the resultant hybridoma cells have the ability of producing hCSF: The use of a well established human lymphoblastoid cell line which can be readily subcultured is more efficient for the mass production of hCSF, since such established cell line can be multiplied more rapidly, and usually exhibits a several to several ten times higher hCSF-producing ability. Such human lymphoblastoid lines are obtainable by establishing in a suitable manner human lymphoblastoid cells from a patient suffering from a leukemia, e.g. acute lymphatic leukemia, chronic myelogenous leukemia, or acute myelogenous leukemia, malignant lymphoma, Burkitt lymphoma, or infectious mononucleosis. Human lymphoblastoid lines usable may be obtained by transforming normal human lymphocytes by use of a suitable carcinogenic virus, agent or irradiation, such as Epstein-Barr virus (EB virus), mitogen or x-ray irradiation, and establishing the obtained lymphoblastoid cells. Examples of such lines are B-Ta, Q-Ta, B-Ue, Q-Ue, B-Ke, and Q-Ku, reported in *Protein, Nucelic Acid and Enzyme,* vol. 20, No. 6, pp. 616–643 (1975). Preferably, the human lymphoblastoid line is of leukemic origin as, for example, Namalva, reported by Strander, H. et al, *Journal of Microbiology,* vol. 1, pp. 116–117 (1975), BALL-1, TALL-1, and NALL-1, reported by Miyoshi, I. et al, *Nature,* vol. 267, No. 4614, pp. 843–844 (1977), or JBL reported by Miyoshi, I. et al, *Cancer,* vol. 40, pp. 2999–3003 (1977). Other lymphoblastoid cell lines usable include the other human lymphoblastoid cell lines listed in the above cited Strander et al publication, including Akuba, P3HR-1 and LY-46. Others include the cell lines of M-7002 and B-7101 as described in *Journal of Immunology,* vol. 113, pp. 1334–1345 (1974); EBV-Sa, EBV-Wa, MOLT-3 and EBV-HO, as described in *The Tissue Culture,* vol. 6, No. 3, pp. 527–546 (1980); CCRF-SB (ATCC CCL 120); BALM 2; DND-41; etc. Since transplantation of the above mentioned well established human lymphoblastoid cell line into a non-human warm-blooded animal body results in the formation of a massive tumor, and said massive tumor is hardly contaminated with the host animal cells, the multiplied viable human lymphoblastoid cells can be easily isolated from the host animal and also readily disaggregated.

As to the fusion of human lymphoblastoid cells with above mentioned human cells capable of producing hCSF, any fusion techniques can be used in the present invention. For example, the HVJ methods such as, the Erythrocyte-ghost-fusion method, those with ribosome associated with HVJ spikes and those attained with the addition of HVJ, and the method using polyethylene glycol can be employed conveniently in the present invention. References which disclose methods of cell fusion include Yamanaka, T. et al, *Biken Journal,* vol. 9, pp. 159–175 (1966), or Pontecorvo, G., *Somatic Cell Genet.,* vol. 1, No. 4, pp. 397–400 (October 1975), the contents of which are hereby incorporated by reference. The cell fusion inducing agent which may be used in this process may be any agent which will induce cell fusion, preferably Sendai virus or polyethylene glycol.

The genetic sites coding for the production of hCSF can be introduced into human lymphoblastoid cells by gene recombinant techniques with DNA ligase, nuclease and DNA polymerase to exhibit similar effects to those attained by the above mentioned cell fusion technique.

As to the animals usable in the present invention, any animal can be used according to the invention so far as the hybridoma cells can multiply therein. For example, poultry such as, chicken and pigeon, and mammalian such as dog, cat, monkey, goat, pig, cow, horse, rabbit, guinea pig, rat, hamster, mouse and nude mouse are all advantageously usable in the present invention.

Since such cell transplantation elicits undesirable immunoreaction in the animal, the use of a newborn or infant animal, or those in the youngest possible stage, for example, egg, embryo or foetus, is desirable.

In order to reduce the immunoreaction, the animal can be treated, prior to the cell transplantation, with irradiation, of about 200 to 600 rem of X-ray or γ-ray, or with injection of antiserum or immunosuppressive agent prepared according to conventional methods. Since nude mouse, when used as the host animal, exhibits less immunoreaction even in its adulthood, any established human cell lines can be conveniently and easily transplanted and multiplied therein without such pretreatment.

Stabilization of the hybridoma cell multiplication and augmentation of hCSF production can be both attained by repeated cell transplantation procedure using combination(s) of different non-human warm-blooded animals; for example, the hybridoma cells may be implanted and multiplied firstly in hamster, then the multiplied hybridoma cells can be reimplanted in another animal, for example, nude mouse. Furthermore, the repeated transplantation as described above can be carried out effectively with animals of the same class or division as well as with those of the same species or genus.

As to the sites in the host animal where the hybridoma cells are implantable, the cells can be implanted in any site of the host animal body so far as the hybridoma cells multiply therein, and also the hybridoma cells can be implanted in the allantoic cavity, or intravenously, intraperitoneally or subcutaneously.

Besides direct cell transplantation of the hybridoma cells into the animal body, any of the conventional hybridoma cell lines capable of producing hCSF can be multiplied while utilizing the nutrient body fluid supplied from the animal body by embedding, for example, intraperitoneally, in the animal body a conventional diffusiion chamber, of any of various shapes and sizes, and equipped with a porous membrane filter, ultra filter, or hollow fiber with pore sizes of about $10^{-7}$ to $10^{-5}$ m in diameter which prevents contamination of the diffusion chamber with host cells and allows the animal to supply its nutrient body fluid to the hybridoma cells. Additionally, the diffusion chamber can be designed, if necessary, so it could be placed, for example, on the host animal, and the body fluid allowed to circulate from the animal body into the chamber, to enable observation of the cell suspension in the chamber through transparent side window(s) equipped on the chamber wall(s), and to enable replacement and exchange with a fresh chamber. Cell multiplication thereby increases to a further higher level over the period of the animal life and the hybridoma cell production per animal is further augmented without sacrificing the host animal. Furthermore, when such diffusion chamber is used, since the multiplied hybridoma cells can be harvested easily and no immunoreaction is elicited due to the absence of direct contact of hybridoma cells with the host animal cells, any non-human warm-blooded animal can be used as the host in the invention without any pretreatment to reduce the immunoreaction.

Feeding of the host animal implanted with the hybridoma cells can be carried out easily by conventional methods even after the cell transplantation, and no special care is required.

The period required to obtain the maximum cell multiplication in the host animal is usually one to 20 weeks. However, when an established hybridoma cell line is implanted in the host animal, the maximum cell multiplication of such established hybridoma cell line can be attained within one to five weeks after the cell transplantation due to its much higher cell multiplication rate.

According to the present invention, the number of the hybridoma cells obtained per host animal is about $10^7$ to $10^{12}$ or more. In other words, the number of the hybridoma cells transplanted into the animal body increases about $10^2$ to $10^7$ fold or more, corresponding to about 10 to $10^6$ fold or more than that attained by in vitro tissue culture method using nutrient medium; thus, the hybridoma cells are conveniently usable for hCSF production.

As to the method for release of hCSF from the multiplied hybridoma cells, any method can be employed so far as the hybridoma cells obtained by the above mentioned procedure release hCSF thereby. For example, the multiplied hybridoma cells, obtained by multiplying the cells in ascite in suspension and harvesting them from said ascite, or by extracting the massive tumor formed subcutaneously and harvesting them after disaggregation of said massive tumor, are suspended in a concentration of about $10^4$ to $10^8$ cells per ml in a nutrient medium, kept at a temperature of about 20° to 40° C., and then incubated at this temperature for about one to a few weeks to produce hCSF. In order to increase hCSF production from the hybridoma cells, any hCSF inducing agent could be added to the above mentioned nutrient medium. For example, those agents which have been well known to the public, such as natural double stranded RNA; synthetic double stranded RNA such as Poly I:C; microbial lipopolysaccharides; mitogens such as phytohemagglutinin, cancanavalin A, tuberculin(PPD) or pokeweed mitogen; chemically modified polymer such as dextran sulfate; synthetic polymer such as pyran copolymer or polyacrylic acid; various cationic low molecular compounds; various endotoxins; and lithium compounds such as $Li_2CO_3$ or LiCl, are all conveniently usable as hCSF inducer in the invention.

The hCSF thus obtained can be collected easily by purification and separation using conventional techniques such as salting-out, dialysis, filtration, centrifugation, concentration and lyophilization. If a further purified hCSF is desirable, an hCSF preparation with the highest purity can be obtained by the above mentioned techniques in combination with conventional techniques such as adsorption and desorption with ion exchange, fractionation by molecular weight, affinity chromatography, isoelectric point fractionation and electrophoresis.

Since the hCSF preparation thus obtained is immunologically and physiochemically identical with those obtained from human tissue culture by conventional methods, and it is less contaminated with hepatitis virus or pyrogens than the hCSF preparation obtained from serum or urine, it is advantageously usable, as a drug, alone or in combination with one or more agents for the prevention and treatment of human diseases.

All determination of hCSF production in the SPECIFICATION were performed according to the assay method using mouse bone marrow cells as described by S. Asano et al., (Br. J. Cancer, Vol. 41, pp. 689–694 (1980). As defined in the report, one unit of hCSF forms one colony from $5 \times 10^4$ mouse bone marrow cells in 0.1 ml of the test sample preparation.

The following description illustrates some embodiments of the information for carrying out the process of this invention; it is not to be construed as limiting the scope of the invention.

EXAMPLE 1

Minced and disaggregated human lung carcinoma cells extracted from a lung carcinoma patient and a human Namalwa leukemic lymphoblastoid cell line were suspended in a vessel with a salt solution containing 140 mM NaCl, 54 mM KCl, 1 mM $NaH_2PO_4$ and 2 mM $CaCl_2$ to give a respective cell concentration of about $10^3$ per ml, and the cell suspension was mixed with a fresh preparation of a salt solution with the same composition and containing UV-preinactivated Sendai virus under ice-chilling conditions. Five minutes after the mixing, the mixed suspension was placed in a 37° C. incubator and incubated for 30 minutes therein with agitation to effect cell fusion and introduction of the ability of producing hCSF into the human Namalwa lymphoblastoid line. After cloning the hybridoma cell line capable of producing hCSF according to the conventional method, the hybridoma cell line was transplanted intraperitoneally in adult nude mice and the nude mice were fed for five weeks in the usual way. The massive tumors, about 14 grams each, formed in the host animal bodies, were extracted and then suspended in a saline solution containing trypsin to disaggregate said massive tumors. After disaggregated cells were washed with RPMI 1640 medium, pH 7.2, supplemented with 10 v/v% foetal bovine serum, the cells were resuspended in a fresh preparation of the same medium to a cell concentration of about $1 \times 10^5$ per ml and incubated therein at 37° C. for seven days to release hCSF while replacing periodically the medium with fresh medium. At the end of the incubation period, the suspension was treated supersonically and the supernatant of the suspension was assayed for its hCSF. The level of hCSF was about 2,500 units per ml of the suspension.

As a control test, unfused human lung carcinoma cells were treated similarly as described above to release hCSF. The hCSF production from said cells was only 120 units per ml of the suspension.

In addition, the above mentioned hybridoma cell line and the human lung carcinoma cells were suspended and incubated separately in vitro in RPMI 1640 medium, pH 7.2, supplemented with 10 v/v% foetal bovine serum, at 37° C. and then treated individually in the same way as described above to release hCSF. The levels of hCSF in the media were respectively only about 95 units and 85 units per ml of the cell suspension, which were even lower than that attained from the above mentioned control test.

In order to compare the hCSF productivity of the hybridoma cell according to the invention with the hCSF productivity of a fibroblastoid hybridoma cell using the same hCSF producing human cell, the following control experiments were conducted. The human lung carcinoma cells were fused with a human lung fibroblastoid cell line, WI-26, ATCC CCL 95, similarly as in the above. The obtained hybridoma cells capable of producing hCSF were cultured in vitro in RPMI 1640 medium (pH 7.2), supplemented with 10 v/v % fetal bovine serum, at 37° C. for seven days to produce hCSF, similarly as above. The hCSF production was only about 15 units per ml of the cell suspension.

Separately, the fibroblastoid hybridoma cells were implanted intraperitoneally into adult nude mice, which were then fed in the usual way for five weeks. The resultant massive tumors, about 3 g each, were extracted, disaggregated, and cultured in vitro similarly as in Example 1 to product hCSF. The hCSF production so obtained was only 20 units per ml of cell suspension.

EXAMPLE 2

A human NALL-1 leukemic lymphoblastoid cell line wherein the ability of producing hCSF of human B-lymphocytes was introduced according to the procedure as described in EXAMPLE 1, was transplanted subcutaneously into newborn hamsters, pretreated with antiserum prepared from rabbit according to a conventional method in order to reduce the immunoreaction. After three-week feeding of the newborn hamsters bearing the human cells, the massive tumors, about 9 grams each, formed subcutaneously in the hamsters were extracted and then treated in the same manner as described in EXAMPLE 1 to release hCSF. The hCSF production was about 3,500 units per ml of the cell suspension.

EXAMPLE 3

According to the cell fusion technique as described in EXAMPLE 1, the ability of producing hCSF of human submaxillary gland tumor cells derived from a patient with submaxillary tumor was introduced into a human JBL leukemic lymphoblastoid cell line. After cloning the hybridoma cell line capable of producing hCSF according to a conventional method, the hybridoma cell line capable of producing hCSF was transplanted intravenously into newborn rats. The rats bearing the hybridoma cell line were fed for four weeks in the usual way. The resultant massive tumors, about 37 grams each which formed in the rats, were removed and treated similarly as described in EXAMPLE 1 to release hCSF. The hCSF production was about 2,900 units per ml of the cell suspension.

EXAMPLE 4

An additional test was carried out in a similar manner as described in EXAMPLE 3 to release hCSF, except that about 10 µg of phytohemagglutinin per ml of the culture medium was added to the medium in this test. The hCSF production was about 4,500 units per ml of the cell suspension.

EXAMPLE 5

A human TALL-1 leukemic lymphoblastoid cell line was fused with gastric carcinoma cells derived from a patient with gastric carcinoma by a conventional cell fusion technique using polyethylene glycol. After cloning the hybridoma cell line capable of producing hCSF according to a conventional method, the hybridoma cell line was transplanted subcutaneously into adult mice which had been immunosuppressed by γ-irradiation of about 400 rem. After four-weeks of feeding the mice in the usual way, the massive tumors, about 15 grams each, formed subcutaneously in the mice, were extracted and treated in the same way as described in EXAMPLE 1 to release hCSF. The hCSF production was about 3,500 units per ml of the cell suspension.

EXAMPLE 6

A human TALL-1 leukemic lymphoblastoid cell line wherein the ability of producing hCSF of human kidney carcinoma cells derived from a kidney carcinoma patient was introduced by the same cell fusion technique as described in EXAMPLE 5, was suspended into a saline solution in a 10 ml cylindrical plastic diffusion chamber equipped with a porous membrane filter, pore size about $0.5\mu$. Then the diffusion chamber containing the cell suspension was embedded intraperitoneally in an adult rat, and after four weeks of usual feeding, the chamber was removed from the rat. The cell concentration thus obtained in the chamber was about $2\times10^9$ per ml, which was almost $10^3$ fold or more higher than that attained by cultivating in vitro the cells in a $CO_2$ incubator. The hCSF production attained by treating the multiplied cells in the same manner as described in EXAMPLE 1 was about 4,200 units per ml of the cell suspension.

The following control experiment was conducted to show the hCSF productivity of the hybridized TALL-1, as compared with the hCSF productivity of the intact human kidney carcinoma cells, after the in vivo multiplication with such diffusion chamber. The human kidney carcinoma cells were suspended in a saline solution and transferred into a 10 ml cylindrical plastic diffusion chamber equipped with a porous membrane filter having a nominal pore size of about $0.5\mu$. The diffusion chamber was then embedded intraperitoneally into an adult rat, and, after four weeks of usual feeding, the chamber was removed from the animal. The density in the chamber attained by the above operation was about $5.5\times10^6$ cells per ml. The obtained human cells were then treated similarly as in Example 1 to produce hCSF. The hCSF production was about 195 units per ml of the cell suspension.

EXAMPLE 7

The human TALL-1 leukemic lymphoblastoid cell line was fused similarly as in EXAMPLE 6 and was treated similarly as in EXAMPLE 1 to release hCSF, except that about 5 µg of synthetic double stranded RNA, Poly I:C, was added to the medium in this test. The hCSF production was about 7,300 units per ml of the suspension.

EXAMPLE 8

A human Namalwa leukemic lymphoblastoid cell line wherein the ability of producing hCSF was introduced similarly as in EXAMPLE 1 was implanted in allantoic cavities of embryonated eggs which had been preincubated at 37° C. for five days. After the incubation of the eggs at this temperature for an additional one week, the multiplied human cells were harvested and treated similarly as in EXAMPLE 1 to induce hCSF, except that about 10 µg of tuberculin PPD was added to the medium in this test. The hCSF production was about 5,700 units per ml of the suspension.

EXAMPLE 9

A normal human lymphoblastoid cell line, B-Ta, obtained by transforming normal human lymphocytes with EB virus, was fused with human gastric carcinoma cells similarly as in Example 1. The obtained hybridoma cells capable of producing hCSF were implanted intraperitoneally into adult nude mice, and the animals were then fed in the usual way for five weeks. The resultant massive tumors, about 9 g each, were disaggregated by extracting, mincing and suspending in a physiological saline solution containing trypsin. The multiplied cells so obtained were cultured in vitro similarly as in Example 1 to produce hCSF. The hCSF level was about 1,500 units per ml of the cell suspension.

It will be obvious to those skilled in the art that various changes may be made without departing from the scope of the invention and the invention is not to be considered limited to what is described in the specification.

What we claim is:

1. In a process for producing human colony stimulating factor (hCSF) which comprises culturing human cells capable of producing hCSF on a culture medium under conditions appropriate to accumulate a substantial amount of hCSF, and recovering the accumulated hCSF from the culture, the improvement whereby the hCSF production can be extremely enhanced, wherein said human cells capable of producing hSCF are obtained by the process comprising:

implanting hCSF-producing hybridoma cells, which are hybrids of hCSF-producing human cells and human lymphoblastoid cells, in an immunodeficient or immunosuppressed non-human warm-blooded animal;

feeding the animal to allow said hybridoma cells to utilize the nutrient body fluid of the animal for their multiplication; and extracting and disaggregating the resultant rumor, formed in the animal, to obtain the multiplied hybridoma cells.

2. A process in accordance with claim 1, wherein said hCSF-producing human cells are human lung carcinoma cells.

3. A process in accordance with claim 1, wherein said hCSF-producing human cells are human B-lymphocytes.

4. A process in accordance with claim 1, wherein said hCSF-producing human cells are human submaxillary gland tumor cells.

5. A process in accordance with claim 1, wherein said hCSF-producing human cells are human gastric carcinoma cells.

6. A process in accordance with claim 1, wherein said hCSF-producing human cells are human kidney carcinoma cells.

7. A process in accordance with claim 1, wherein said human lymphoblastoid cells are of leukemic origin.

8. A process in accordance with claim 1, wherein said human lymphoblastoid cells are selected from the group consisting of Namalva, JBL, BALL-1, NALL-1 and TALL-1 cells.

9. A process in accordance with claim 1, wherein said non-human warm-blooded animal is a fowl or a mammalian.

10. A process in accordance with claim 1, wherein said non-human warm-blooded animal is a member selected from the group consisting of chicken, pigeon, dog, cat, monkey, goat, pig, cow, horse, guinea pig, rabbit, rat, hamster, nude mouse or mouse.

11. A process in accordance with claim 1, wherein said hybridoma cells are obtained by:

suspending hCSF-producing human cells together with human lymphoblastoid cells in a salt solution containing an effective amount of a cell fusion inducing agent;

allowing the resultant cell suspension to stand for a period sufficient to effect cell fusion; and selecting or cloning hybridoma cells which produce hCSF.

12. A process in accordance with claim 11, wherein said cell fusion inducing agent is an inactivated Sendai virus or polyethylene glycol.

13. In a process for producing human colony stimulating factor (hCSF) which comprises culturing human cells capable of producing hCSF on a culture medium under conditions appropriate to accumulate a substantial amount of hCSF, and recovering the accumulated hCSF from the culture, the improvement whereby the hCSF production can be extremely enhanced, wherein said human cells capable of producing hCSF are obtained by the process comprising:

suspending hCSF-producing hybridoma cells, which are hybrids of hCSF-producing human cells and human lymphoblstoid cells, in a device in which the nutrient body fluid of a non-human warm-blooded animal can be supplied to said hybridoma cells;

embedding or placing said device in or on a non-human warm-blooded animal in a manner such that the nutrient body fluid of said animal is supplied to the hybridoma cells within said device;

feeding said animal to allow said hybridoma cells to utilize the nutrient body fluid for their multiplication; and harvesting the multiplied hybridoma cells from the device.

14. A process in accordance with claim 13, wherein said hCSF-producing human cells are human lung carcinoma cells.

15. A process in accordance with claim 13, wherein said hCSF-producing human cells are human B-lymphocytes.

16. A process in accordance with claim 13, wherein said hCSF-producing human cells are human submaxillary gland tumor cells.

17. A process in accordance with claim 13, wherein said hCSF-producing human cells are human gastric carcinoma cells.

18. A process in accordance with claim 13, wherein said hCSF-producing human cells are human kidney carcinoma cells.

19. A process in accordance with claim 13, wherein said human lymphoblastoid cells are of leukemic origin.

20. A process in accordance with claim 13, wherein said human lymphoblastoid cells are selected from the group consisting of Namalva, JBL, BALL-1, NALL-1 and TALL-1 cells.

21. A process in accordance with claim 13, wherein said non-human warm-blooded animal is a fowl or a mammalian.

22. A process in accordance with claim 13, wherein said non-human warm-blooded animal is a member selected from the group consisting of chicken, pigeon, dog, cat, monkey, goat, pig, cow, horse, guinea pig, rabbit, rat, hamster, nude mouse or mouse.

23. A process in accordance with claim 13, wherein said device is a diffusion chamber equipped with a membrane filter, ultra filter or hollow fiber having a nominal pore size in the range of $10^{-7}$–$10^{-5}$ m.

24. A process in accordance with claim 13, wherein said hybridoma cells are obtained by:

suspending hCSF-producing human cells together with human lymphoblastoid cells in a salt solution containing an effective amount of a cell fusion inducing agent;

allowing the resultant cell suspension to stand for a period sufficient to effect cell fusion; and selecting or cloning hybridoma cells which produce hCSF.

25. A process in accordance with claim 24, wherein said cell fusion inducing agent is an inactivated Sendai virus or polyethylene glycol.

* * * * *